United States Patent [19]

Asbeck et al.

[11] 4,250,050
[45] Feb. 10, 1981

[54] SULFOSUCCINATE EMULSIFIERS

[75] Inventors: Adolf Asbeck; Michael Eckelt, both of Dusseldorf; Werner Erwied, Monheim; Rudi Heyden, Erkrath; Manfred Petzold, Dusseldorf, all of Fed. Rep. of Germany

[73] Assignee: Henkel Kommanditgesellschaft auf Aktien, Dusselforf-Holthausen, Fed. Rep. of Germany

[21] Appl. No.: 865,881

[22] Filed: Dec. 30, 1977

[30] Foreign Application Priority Data

Jan. 3, 1977 [DE] Fed. Rep. of Germany ....... 2700072

[51] Int. Cl.³ .................... B01F 17/10; C07C 143/18
[52] U.S. Cl. ............... 252/354; 260/29.6 R; 260/513 B; 526/214; 526/911; 560/151
[58] Field of Search ........................ 252/354; 560/151; 260/513 B; 526/214, 911

[56] References Cited

U.S. PATENT DOCUMENTS

| | | | |
|---|---|---|---|
| 3,329,640 | 7/1967 | Scotti et al. | 252/354 X |
| 3,888,910 | 6/1975 | Smeets | 260/513 B X |
| 3,928,422 | 12/1975 | Sundby | 252/354 X |
| 3,947,400 | 3/1976 | Burkhard et al. | 252/354 X |
| 4,117,237 | 9/1978 | Longley et al. | 252/354 X |

*Primary Examiner*—Richard D. Lovering
*Attorney, Agent, or Firm*—Hammond & Littell, Weissenberger and Muserlian

[57] ABSTRACT

Sulfosuccinic acid derivatives having the formula:

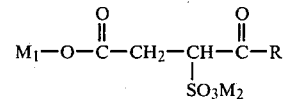

wherein R is a member selected from the group consisting of:

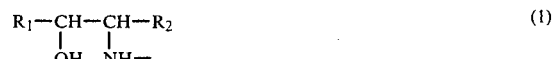

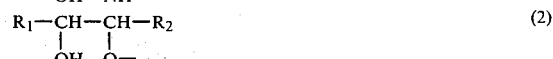

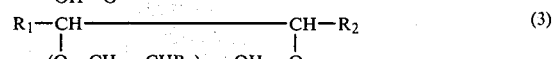

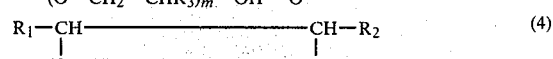

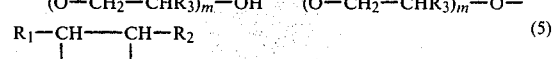

and

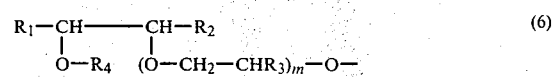

where $R_1$ and $R_2$ are members selected from the group consisting of hydrogen and alkyl having from 1 to 16 carbon atoms, and the sum of the carbon atoms in $R_1$ and $R_2$ is from from 9 to 16, $R_3$ is a member selected from the group consisting of hydrogen and methyl, $R_4$ is alkyl having 1 to 5 carbon atoms, $M_1$ and $M_2$ are cations selected from the group consisting of alkali metals, ammonium, alkylammonium having 1 to 4 carbon atoms in the alkyl and alkylolammonium having 2 to 4 carbon atoms in the alkylol and m is an integer from 1 to 10. These sulfosuccinic acid derivatives are useful as emulsifying agents, particularly in the production of emulsion polymers.

4 Claims, No Drawings

SULFOSUCCINATE EMULSIFIERS

BACKGROUND OF THE INVENTION

The production of emulsion polymers from olefinically unsaturated monomers requires the use of emulsifying agents by means of which, during polymerization, the monomers to be polymerized, and the polymers which have been formed, are dispersed in the aqueous phase in a finely-divided and stable manner. The dispersions must have a particle size which is as uniform as possible and should have a high degree of stability relative to mechanical influences, additives or electrolytes, dyestuffs and changes of temperature. The requirements in this respect are high since, during storage and transportation, and during further processing to form adhesives, dispersion dyes, coatings and linings, the emulsion polymers are subjected to a large number of influences and demands which can lead to the breakdown of the emulsions. In particular, great importance is attached to adequate resistance to change of temperature, wherein the emulsion should resist repeated freezing and thawing without damage. A number of different emulsifying agents have been employed in the production of emulsion polymers. Sulfosuccinic acid derivatives, such as sodium dihexyl sulfosuccinate and disodium coconut fatty acid-monoethanolamido-sulfosuccinate give good polymer emulsions of low particle size but these emulsions are not stable to alternating freezing and thawing.

OBJECTS OF THE INVENTION

An object of the present invention is to develop sulfosuccinic acid derivatives which give emulsion polymers which have improved properties and especially improved resistance to breakdown in repeated freezings and thawings.

Another object of the present invention is the development of sulfosuccinic acid derivatives having the formula:

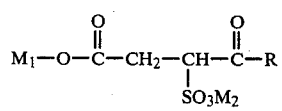

wherein R is a member selected from the group consisting of:

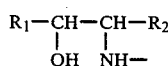 (1)

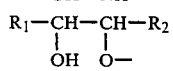 (2)

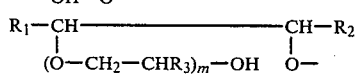 (3)

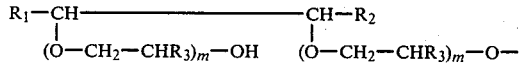 (4)

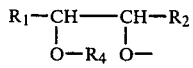 (5)

and $$R_1-CH\text{------}CH-R_2 \atop | \quad\quad\quad | \atop O-R_4 \quad (O-CH_2-CHR_3)_m-O- \quad\quad (6)$$

where $R_1$ and $R_2$ are members selected from the group consisting of hydrogen and alkyl having from 1 to 16 carbon atoms, and the sum of the carbon atoms in $R_1$ and $R_2$ is from from 9 to 16, $R_3$ is a member selected from the group consisting of hydrogen and methyl, $R_4$ is alkyl having 1 to 5 carbon atoms, $M_1$ and $M_2$ are cations selected from the group consisting of alkali metals, ammonium, alkylammonium having 1 to 4 carbon atoms in the alkyl and alkylolammonium having 2 to 4 carbon atoms in the alkylol and m is an integer from 1 to 10.

A further object of the present invention is the development of freeze-thaw stable emulsion polymers and the process of preparing the same employing the above sulfosuccinic acid derivatives.

These and other objects of the present invention will become more apparent as the description thereof proceeds.

DESCRIPTION OF THE INVENTION

The above objects have been achieved by the present invention which provides novel sulfosuccinic acid derivatives of the general formula:

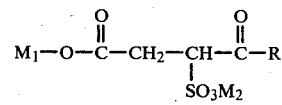

wherein R represents:

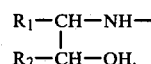

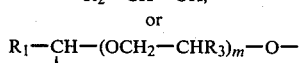

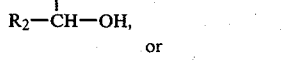

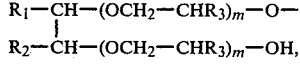

$R_1$ and $R_2$ each independently represent H or an alkyl radical having 1 to 16 carbon atoms, the total of the carbon atoms in $R_2$ and $R_3$ being 9 to 16, $R_3$ represents H or $CH_3$, $R_4$ represents an alkyl radical having 1 to 5 carbon atoms, $M_1$ and $M_2$ each represent Na, K, $NH_4$ or the cation of an organic base, and m is 0 or an integer from 1 to 10.

More particularly the present invention relates to sulfosuccinic acid derivatives having the formula:

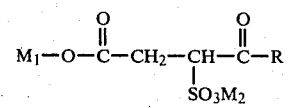

wherein R is a member selected from the group consisting of:

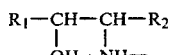 (1)

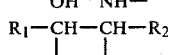 (2)

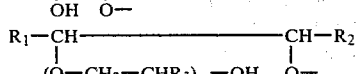 (3)

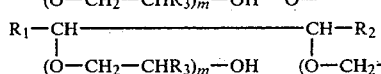 (4)

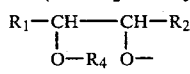 (5)

and

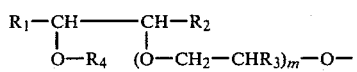 (6)

where $R_1$ and $R_2$ are members selected from the group consisting of hydrogen and alkyl having from 1 1 to 16 carbon atoms, and the sum of the carbon atoms in $R_1$ and $R_2$ is from from 9 to 16, $R_3$ is a member selected from the group consisting of hydrogen and methyl, $R_4$ is alkyl having 1 to 5 carbon atoms, $M_1$ and $M_2$ are cations selected from the group consisting of alkali metals, ammonium, alkylammonium having 1 to 4 carbon atoms in the alkyl and alkylolammonium having 2 to 4 carbon atoms in the alkylol and m is an integer from 1 to 10.

These sulfosuccinic acid derivatives may be used as emulsifying agents for producing emulsion polymers, particularly polymers and copolymers from (meth)acrylic acid and esters of (meth)acrylic acid.

In the production of the sulfosuccinic acid derivatives of the invention, alcohols or amines derived from terminal or non-terminal olefins having chain lengths in which the total of the carbon atoms is $R_1+R_2+2$ or 11 to 18 are employed.

For the production of the intermediate alcohols or amines derived from olefins, non-terminal or terminal alkenes or olefins are reacted with epoxidizing agents, such as peracetic acid, to give the respective olefin epoxides or epoxyalkanes. By a further reaction with alcohols or ammonia, the corresponding vicinal alkanediols, vicinal hydroxyalkylamines and vicinal alkoxyalkanols, optionally alkoxylated with ethylene oxide and/or propylene oxide, are formed. The vicinal hydroxyalkylamines are described in U.S. patent application Ser. No. 683,319, filed May 5, 1976, now abandoned in favor of continuation application Ser. No. 889,989, filed Mar. 24, 1978, now U.S. Pat. No. 4,181,624, issued on Jan. 1, 1980, particularly those produced from mixtures of non-terminal olefins.

In the preparation of the above intermediate alcohols or amines, preferably, terminal mono-olefins with 10 to 18 carbon atoms or mixtures of mono-olefins with 10 to 18 carbon atoms containing statistically distributed non-terminal double bonds are employed. These olefin mixtures are known per se and can be obtained, for example, by catalytic dehydration or by chlorination/dehydrochlorination of paraffins having 8 to 24 carbon atoms and selective extraction of the non-terminal mono-olefins obtained. However, it is also possible to use mixtures of such olefins with saturated hydrocarbons, as they are obtained in the preparation of these olefins. Preferred as mixtures of isomeric mono-olefins are the fractions with a high content of linear $C_{11-14}$ olefins or $C_{16-18}$ olefins. The particularly preferred mixtures of non-terminal olefins have the following approximate chain length distribution:

| | | | |
|---|---|---|---|
| (a) Fraction $C_{11-14}$ olefins (distribution in % by weight) | | | |
| $C_{11}$ | Olefins | About | 20–22 |
| $C_{12}$ | " | " | 30 |
| $C_{13}$ | " | " | 26–30 |
| $C_{14}$ | " | " | 20–22 |
| (b) Fraction $C_{15}$-$C_{18}$ olefins | | | |
| $C_{15}$ | Olefins | About | 25–26 |
| $C_{16}$ | " | " | 30–35 |
| $C_{17}$ | " | " | 30–31 |
| $C_{18}$ | " | " | 6–15 |

The above preferred mixtures of $C_{11}$-$C_{14}$ olefins and $C_{15}$-$C_{18}$ olefins can also have deviations in the indicated chain length distributions.

For the preparation of the products according to the invention, the olefin mixtures are epoxidized by means of known methods, for example, with peracetic acid.

Terminal olefins can likewise be reacted to obtain the epoxyalkanes having 10 to 18 carbon atoms, such as 1,2-epoxydecane, 1,2-epoxydodecane, 1,2-epoxytridecane, 1,2-epoxytetradecane, 1,2-epoxyhexadecane and 1,2-epoxyoctadecane. Mixtures of these 1,2-epoxyalkanes can also be employed.

The sulfosuccinic acid derivatives of the present invention are obtained by reacting substantially equimolar amounts of the above vicinal alkanediols, vicinal hydroxyalkylamines and vicinal alkoxyalkanols or their alkylene oxide adducts with maleic acid anhydride and sodium bisulfite. The processing steps required to produce the compounds are known in principle. The production of the compounds is described in the following examples.

The sulfo-succinic acid derivatives are especially suitable as emulsifying agents for producing polymers or copolymers from acrylic acid, methacrylic acid, acrylic acid and methacrylic acid esters, vinyl acetate, "Versatic" acid vinyl ester, styrene, vinylchloride, etc. Preferably the monomers are acrylic acid, methacrylic acid, lower alkyl acrylates and lower alkyl methacrylates. 1 to 5 percent by weight of emulsifying agent, relative to the content of monomers, are used. Polymerization is effected in a known manner under thorough agitation at an elevated temperature with the addition of polymerization catalysts, such as ammonium- or potassium peroxydisulfate, benzoyl peroxide, azoisobutyronitrile, etc. The polymerization catalysts are employed in amounts of from 0.02% to 2% by weight of the monomers.

The polymerization charge can also contain molecular weight regulators, such as aliphatic aldehydes, organic nitrocompounds, aliphatic mercaptans or chlorohydrocarbons.

The addition of the monomers can be done in various ways. Thus, for instance, all monomers may be pre-emulsified in an aqueous emulsifier solution and then the whole mixture be charged or only a part of the mixture be charged and the residual mixture added in portions. It is also possible to pre-emulsify only a part of the monomers in the emulsifier solution and to add in portions the residual monomers singly or as a mixture, whereby the proportion of the monomers to each other may be adjusted according to their reactivities.

The pH-value of the polymerization charge is to be between 2 and 10. This can be attained by the addition of buffer substances, such as bicarbonates, carbonates, phosphates, borates, acids, for instance hydrochloric acid, acetic acid, bases, such as ammonia, sodium hydroxide, potassium hydroxide before or during the polymerization.

The charge is polymerized at temperatures between 0° C. and 100° C., preferably 40° C. to 90° C., depending upon the catalyst system.

The polymerization is usually carried out in water-cooled reaction vessels that are generally equipped with stirring devices and deflecting plates. The process may also be carried out continuously.

The dispersions prepared by the claimed process are suitable for coatings and plastering on masonry and wood and as binders for fibrous substances (textile fleeces, cellulose fibers, leather cuttings) are further suitable for the preparation of coating materials for paper, leather, wood, sound absorbers, fillers and as adhesives.

Particularly suitable sulfosuccinic acid derivatives have proved to be those in which the vicinal hydroxyamine group or the vicinal diol- or hydroxy ether group is statistically distributed over the olefin chain, the olefin having a chain length distribution of from 11 to 14 or from 15 to 18 carbon atoms.

The following examples are illustrative of the invention without being limitative in any manner.

In the following examples, PW signifies "parts by weight."

EXAMPLE 1

The vicinal hydroxyamine used as a starting material is a derivative, derived from a nonterminal olefin epoxide, having the following carbon chain distribution:
Approximately 20% $C_{11}$
Approximately 30% $C_{12}$
Approximately 30% $C_{13}$
Approximately 20% $C_{14}$
This vicinal hydroxyamine is produced following the process of Example 1 of Ser. No. 683,319, now abandoned.

98.0 PW of maleic acid anhydride were introduced into and melted in a vessel provided with an agitator, reflux cooler, thermometer and gas inlet pipe for nitrogen. Thereafter, 224 PW of the above vicinal hydroxyamine were stirred in at 50° C. with the simultaneous introduction of nitrogen. The temperature is maintained between 50° C. and 60° C. while the hydroxyamine was being added, and was then increased to 95° C. to 100° C. The reaction mixture was agitated at this latter temperature for 40 to 45 minutes. The temperature was then dropped to 80° C. and 800 PW of an aqueous solution, containing 126.2 PW of sodium sulfite, was added drop by drop within 15 to 20 minutes. The mixture was agitated at 80° C. for a further 30 to 40 minutes and was decanted after cooling.

The product obtained is an approximately 40% aqueous emulsifier solution which is clearly miscible with water in any ratio (Emulsifying Agent I).

EXAMPLE 2

In the manner described in Example 1, 82.5 PW of a vicinal hydroxyamine, derived from a nonterminal olefin epoxide, and having the following approximate carbon chain distribution:
25% $C_{15}$
30% $C_{16}$
30% $C_{17}$
15% $C_{18}$
(substantially produced following Example 2 of Ser. No. 683,319, now abandoned) were first reacted with 29.4 PW of maleic acid anhydride and then with 262.6 PW of an aqueous solution containing 37.9 PW of sodium sulfite.

An approximately 40% clear, aqueous solution is obtained (Emulsifying Agent II).

EXAMPLE 3

In the apparatus described in Example 1, 49 PW of finely powdered maleic acid anhydride were first added in portions, commencing at 55° C., to 138.5 PW of an alcohol produced from ethylene glycol and a nonterminal olefin epoxide having the following approximate carbon chain distribution:
20% $C_{11}$     30% $C_{13}$
30% $C_{12}$     20% $C_{14}$
The reaction temperature was subsequently increased to approximately 100° C. within 30 minutes and the mixture is maintained this temperature under agitation for a further 30 minutes.

Finally, after cooling to 70° C., 642.5 PW of an aqueous solution containing 63.1 PW of sodium sulfite were added under agitation for a period of 30 1 minutes. The mixtures was taken agitated at 70° C. to 80° C. for 30 to 45 minutes and then cooled to 25° C.

A bright, clearly water-soluble reaction product having a 30% content of emulsifying agent is obtained (Emulsifying Agent III).

EXAMPLE 4

In the same manner as described in Example 3, 78.8 PW of an alcohol, produced from ethylene glycol and an α-olefin epoxide having the approximate carbon chain distribution:
25% $C_{15}$     30% $C_{17}$
30% $C_{16}$     15% $C_{18}$
were further reacted in the first instance with 24.5 PW of maleic acid anhydride and subsequently with 32 PW of sodium sulfite in 315 PW of water (Emulsifying Agent IV).

EXAMPLE 5

256.8 PW of an alcohol, produced from ethylene glycol and a terminal olefin epoxide having the following approximate carbon chain distribution:
60% $C_{12}$
40% $C_{14}$
were introduced into the apparatus already described and were mixed with 98.1 PW of maleic acid anhydride under agitation at 80° C. to 100° C. and converted into the corresponding monoester derivative under further agitation for half an hour at 100° C.

1500.0 PW of an aqueous solution with 244.7 PW of sodium triethanol ammonium sulfite were subsequently added at a temperature of from 70° C. to 75° C., and the mixture was agitated for 45 minutes at 80° C. Thereafter it was made up to 2000 PW with 145.5 PW of water and cooled.

A clear solution having a 30% content of emulsifying agent is obtained.

EXAMPLE 6

An emulsion polymer was produced in a heatable reaction vessel having an agitator, a reflux cooler and a tube for introducing nitrogen. The reaction boiler was connected by way of regulating valves to two reservoirs which are arranged at a greater height, one of which reservoirs was also provided with an agitator.

The following were required for one preparation:

```
478.0  PW of distilled water
480.0  PW of n-butyl acrylate
  9.6  PW of methacrylic acid
 30.0  PW of emulsifying agent solution
  1.2  PW of ammonium peroxydisulfite, 98% pure
  1.2  PW of sodium disulfite, p.a. 98%
1000.0 PW
```

2.45% on a solids content of the Emulsifying Agents I to IV manufactured in accordance with Examples 1 to 4, and in comparison therewith, known emulsifying agents used for emulsion polymerization, such as sodium dihexyl sulfosuccinate (Emulsifying Agent V), and disodium sulfosuccinate of coconut fatty acid monoethanol amide (Emulsifying Agent VI), were used based on the monomeric proportions during polymerization and were added in the stated dilution. The ammonium peroxydisulfite and the emulsifying agent were dissolved in 428 PW of water and 100 PW of this solution was introduced into the reaction vessel.

The n-butyl acrylate and the methacrylic acid were added to the remaining solution under agitation and were emulsified intensively for 15 minutes. 100 PW of this emulsion were then introduced into the reaction vessel, and the remaining quantity was introduced into the dosing container with agitator where it is agitated continuously. Sodium disulfite was dissolved in 50 PW of water and this solution was introduced into the second dosing reservoir. The emulsion of the monomers introduced into the reaction vessel was now purged for 30 minutes with nitrogen.

15 PW of sodium disulfite solution were then added under the permanent introduction of nitrogen and the reaction mixture was slowly heated. Polymerization commenced at 60° C. to 65° C. with the emission of heat. The temperature, then increasing rapidly, had to be maintained at approximately 77° C. by cooling. The continuous addition of monomer emulsion and sodium disulfite solution commenced during the rise in temperature and should be completed within 1.5 to 2 hours. The temperature should be maintained between 76° C. to 78° C. during this period of time. The mixture was subsequently further agitated for one hour at the same temperature and was then cooled. The pH value is adjusted to approximately 8 with 25% ammonia solution. Only moderate agitation must be effected during the entire reaction period. The polymer dispersions obtained are suitable for producing lining compounds.

The polymer dispersions were tested in accordance with known technical application methods. The results are shown in the following Table. The polymer dispersions produced with the Emulsifying Agents I to IV in accordance with the invention have an unexpectedly high freezing and thawing stability while still giving the desired particle size range.

TABLE

| Emulsifying Agent (2.45%) | % Content of Solid Matter in the Dispersion | Freezing/Thawing Stability | Particle Size μ |
|---|---|---|---|
| I | 48.1 | 3 Cycles | 1–0.1 |
| II | 48.9 | 4 Cycles | 0.1–0.05 |
| III | 48.5 | 4 Cycles | 1–0.1 |
| IV | 47.2 | 2 Cycles | 0.1–0.05 |
| V | 47.5 | 1 Cycle | 1–0.1 |
| VI | 49.0 | 1 Cycle | 1–0.1 |

EXAMPLE 7

The following components were reacted in the apparatus described in Example 6:

```
452.2   PW of methacrylic water
448.0   PW of n-butyl acrylate
  8.8   PW of methacrylate acid
 84.0   PW of emulsifying agent solution
  1.12  PW of ammonium peroxy disulfite
  1.12  PW of sodium disulfite
995.24  PW
```

The quantity of Emulsifying Agents I to IV used was 5.52% (solids content) based on the monomeric proportions. The reaction took place in the same manner as described in Example 6. A polymer dispersion suitable for manufacturing adhesives was obtained.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. Sulfosuccinic acid derivatives having the formula:

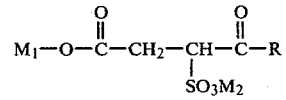

wherein R is

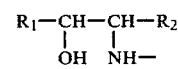

where $R_1$ and $R_2$ are members selected from the group consisting of hydrogen and alkyl having from 1 to 16 carbon atoms, and the sum of the carbon atoms in $R_1$ and $R_2$ is from 9 to 16, $M_1$ and $M_2$ are cations selected from the group consisting of alkali metals, ammonium, alkylammonium having 1 to 4 carbon atoms in the alkyl and alkylolammonium having 2 to 4 carbon atoms in the alkylol.

2. The sulfosuccinic acid derivative of claim 1 wherein $M_1$ and $M_2$ are alkali metal.

3. The sulfosuccinic acid derivative of claim 1 wherein

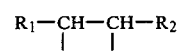

is derived from a nonterminal olefin having the approximate chain length distribution:
$C_{11} = 20\%$
$C_{12} = 30\%$
$C_{13} = 30\%$
$C_{14} = 20\%$.
4. The sulfosuccinic acid derivative of claim 1 wherein
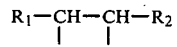
is derived from a nonterminal olefin having the approximate chain length distribution:
$C_{15} = 25\%$
$C_{16} = 30\%$
$C_{17} = 30\%$
$C_{18} = 15\%$.
* * * * *

UNITED STATES PATENT AND TRADEMARK OFFICE
CERTIFICATE OF CORRECTION

PATENT NO. : 4,250,050

DATED : February 10, 1981

INVENTOR(S) : ADOLF ASBECK ET AL.

It is certified that error appears in the above—identified patent and that said Letters Patent is hereby corrected as shown below:

Column 3, line 23: " 1 1 to 16" should read -- 1 to 16 --.

Column 6, line 31: " 30 1 minutes" should read -- 30 minutes --.

Signed and Sealed this

Thirtieth Day of March 1982

[SEAL]

Attest:

Attesting Officer

GERALD J. MOSSINGHOFF

Commissioner of Patents and Trademarks